US011103462B2

(12) United States Patent
Lu et al.

(10) Patent No.: US 11,103,462 B2
(45) Date of Patent: Aug. 31, 2021

(54) PROTEIN NANOCAPSULES WITH DETACHABLE ZWITTERIONIC COATING FOR PROTEIN DELIVERY

(71) Applicant: THE REGENTS OF THE UNIVERSITY OF CALIFORNIA, Oakland, CA (US)

(72) Inventors: Yunfeng Lu, Culver City, CA (US); Jie Li, Los Angeles, CA (US); Yang Liu, Los Angeles, CA (US); Jie Ren, Los Angeles, CA (US); Jing Wen, Culver City, CA (US)

(73) Assignee: The Regents of the University of California, Oakland, CA (US)

( * ) Notice: Subject to any disclaimer, the term of this patent is extended or adjusted under 35 U.S.C. 154(b) by 16 days.

(21) Appl. No.: 16/063,221

(22) PCT Filed: Dec. 14, 2016

(86) PCT No.: PCT/US2016/066713
§ 371 (c)(1),
(2) Date: Jun. 15, 2018

(87) PCT Pub. No.: WO2017/106380
PCT Pub. Date: Jun. 22, 2017

(65) Prior Publication Data
US 2018/0369159 A1      Dec. 27, 2018

Related U.S. Application Data

(60) Provisional application No. 62/269,392, filed on Dec. 18, 2015.

(51) Int. Cl.
| | | |
|---|---|---|
| *A61K 9/51* | (2006.01) | |
| *A61K 38/38* | (2006.01) | |
| *A61K 38/00* | (2006.01) | |

(52) U.S. Cl.
CPC .......... *A61K 9/5138* (2013.01); *A61K 38/385* (2013.01); *A61K 38/00* (2013.01)

(58) Field of Classification Search
CPC ............................. A61K 9/5138; A61K 38/385
See application file for complete search history.

(56) References Cited

U.S. PATENT DOCUMENTS

| | | | |
|---|---|---|---|
| 6,858,673 B1 * | 2/2005 | Sakamoto | .............. A61K 8/042 514/772.4 |
| 2011/0274682 A1 | 11/2011 | Tang et al. | |

(Continued)

FOREIGN PATENT DOCUMENTS

CN          102475891          5/2012

OTHER PUBLICATIONS

Li; "Protein Nanocapsule Based Protein Carriers for Industrial and Medical Applications"; 2015; https://escholarship.org/uc/item/93k6h4dh (Year: 2015).*

(Continued)

*Primary Examiner* — Timothy P Thomas
(74) *Attorney, Agent, or Firm* — Gates & Cooper LLP

(57) ABSTRACT

The invention relates to protein nanocapsules that exhibit material properties that change in different in vivo environments. A zwitterion moiety on the surface of the nanocapsule can protect the protein from opsonization in a first environment, yet uncouples from the protein nanocapsule in a second environment (e.g. at a pH of less than 6.5). In embodiments of the invention, the uncoupled protein nanocarrier is then internalized by mammalian cells (e.g. tumor cells).

7 Claims, 4 Drawing Sheets
(3 of 4 Drawing Sheet(s) Filed in Color)

(56) References Cited

U.S. PATENT DOCUMENTS

| | | |
|---|---|---|
| 2011/0318297 A1 | 12/2011 | Lu et al. |
| 2014/0134700 A1 | 5/2014 | Lu et al. |
| 2014/0186436 A1 | 7/2014 | Yang et al. |
| 2015/0320693 A1 | 11/2015 | Lu et al. |
| 2015/0359752 A1 | 12/2015 | Lu et al. |
| 2017/0354613 A1 | 12/2017 | Lu et al. |
| 2018/0036254 A1 | 2/2018 | Lu et al. |
| 2018/0369159 A1 | 12/2018 | Lu et al. |

OTHER PUBLICATIONS

EScholarship; https://escholarship.org/uc/item/93k6h4dh#metrics; accessed May 21, 2020 (Year: 2015).*

Extended European Search Report dated Jul. 2, 2019 for European Patent Application No. 16876619.4.

PCT International Search Report and Written Opinion dated Apr. 17, 2017, International Application No. PCT/US2016/066713.

Liu, G. Y., et al., Biocompatible and biodegradable polymersomes for pH-triggered drug release. Soft Matter, 2011, vol. 7, pp. 6629-6636.

Salvage, J.P. et al., Novel biocompatible phosphorylcholine-based self-assembled nanoparticles for drug delivery. Journal of Controlled Release. 2005, vol. 104, pp. 259-270.

Giacomelli, C.,et al., Phosphorylcholine-based pH-responsive diblock copolymer micelles as drug delivery vehicles: light scattering, electron microscopy, and fluorescence experiments. Biomacromolecules, 2006, vol. 7, No. 3, pp. 817-828.

Li, L., et al., Synthesis and characterization of dendritic star-shaped Zwitterionic polymers as novel anticancer drug delivery carriers. Journal of Biomaterials Science. Polymer Edition. 2014, vol. 25, Nos. 14-15, pp. 1641-1657.

Xie, L., et al., Bovine serum albumin nanoparticles modified with multilayers and aptamers for pH-responsive and targeted anticancer drug delivery. Journal of Materials Chemistry, 2012, vol. 22, pp. 6053-6060.

Li, J., Protein nanocapsule based protein carriers for industrial and medical applications. Dissertation. UCLA Chemical Engineering 0294, 2015.

* cited by examiner

PROTEIN NANOCAPSULES WITH DETACHABLE ZWITTERIONIC COATING FOR PROTEIN DELIVERY

CROSS REFERENCE TO RELATED APPLICATIONS

This application is a national stage application, filed under 35 U.S.C. § 371, of International Patent Application No. PCT/US2016/066713, filed on Dec. 14, 2016, which claims the benefit under 35 U.S.C. Section 119(e) of U.S. Provisional Patent Application Ser. No. 62/269,392, entitled "PROTEIN NANOCAPSULES WITH DETACHABLE ZWITTERIONIC COATING FOR PROTEIN DELIVERY" filed Dec. 18, 2015, the contents of which are incorporated herein by reference.

TECHNICAL FIELD

The invention relates to proteins disposed in nanocapsules and methods for making and using them.

BACKGROUND OF THE INVENTION

Amongst various cancer therapies, chemotherapy is one of the major treatment modalities along with debulking surgery. Major challenges in chemotherapy are linked to toxicity on healthy proliferating cells. The life threatening side effects caused by the non-specific tissue distribution of drugs have restricted the systemic high dose strategy. Tumor-targeting vectors have been developed for improved efficacy and reduced toxicity by altering the biodistribution of cancer drugs. However, most of these vectors are often cleared out rapidly (with an undesired accumulation commonly in the liver, spleen or kidney) before they can reach the target site. To increase the circulation time and reduce immunogenicity, poly(ethylene glycol) (PEG) coating remains as the golden standard. Particularly in the case of protein therapeutics, modifying the proteins with PEG leads to improved protein stability, prolonged circulation time, and reduced immune response. However, it has been found that approximately 25% of the patients have developed anti-PEG antibodies. Protein therapeutics that are injected are subsequently opsonized by the circulating antibodies and cleared rapidly, thereby still resulting in accelerated blood clearance and reduced efficacy.

Zwitterionic polymers exhibit outstanding biocompatibility and a protein-adsorption-resistant ability due to their superhydrophilicity. Such neutral polymers have been clinically explored as anti-fouling coatings for blood-contacting devices by significantly reducing the surface energy of the coated surface. As disclosed herein, protein nanocapsules that are coupled to zwitterionic molecules have great potential to escape opsonization, increasing accumulation in the tumor site by the enhanced permeability and retention (EPR) effect, and reducing undesired accumulation in the liver and spleen. However, zwitterionic coatings can also prohibit cell-nanocapsule interaction, and thus such nanocapsules cannot be internalized by cancer cells after accumulation at a tumor site.

There has been research studying the use of pH-sensitive polymeric carriers in targeted antitumor drug delivery based on the intrinsic differences between various solid tumors and the surrounding normal tissues in terms of their relative acidity. The extracellular pH (pHe) in most tumors is more acidic (pH 6.5-7.2) than in normal tissues. Acetal and ketal bonds between the cargos and polymeric coating can be cleaved under acidic pH and therefore are of particular interest for tumor targeting delivery. Current methods for pH-responsive tumor target delivery therapeutics are described, for example in Chinese Patent Application CN 102475891 A. However, these methods are mainly based on PEGylation which causes the development of anti-PEG antibodies, resulting in the fast clearance of the nanocarriers. Also, these nanocarriers have only been applied to small molecule drugs and thus there is still a lack of pH-responsive nanocarriers for protein delivery.

The targeted delivery of agents such as therapeutic nanocarriers to localized sites of diseased tissue is one of the hottest fields in nanomedicine. However, the successful delivery of therapeutic and diagnostic agents to tumor sites by nanocarriers faces a number of challenges. One of the major obstacles for applying nanocarriers for tumor site targeting is the fast clearance by the mononuclear phagocyte system (MPS) (also known as the reticuloendothelial system (RES)) due to opsonization of the nanocarrier surface. Therefore, there is an unmet need for nanocapsules and delivery systems that are opsonin adsorption resistant at physiological pH but also provide enhanced cellular uptake at low pH, which can be used for tumor targeted delivery of drugs.

SUMMARY OF THE INVENTION

As disclosed herein, zwitterionic polymers can be coupled to polyallylamine to form protein nanocapsules with reduced surface energies so as to inhibit nanocapsule opsonization and interaction with macrophages. Once accumulated at a tumor site by the enhanced permeability and retention (EPR) effect, typical zwitterionic polymer coated nanocarriers cannot be internalized by the tumor cells, a phenomenon which limits their use. To overcome this limitation, embodiments of the invention further provide protein nanocapsules with detachable zwitterionic polymers. These zwitterionic elements can protect the nanocapsules from macrophage uptake, yet can detach once exposed to a low pH environment (as occurs at tumors and other sites of pathological cell growth), thereby allowing the nanocapsules to be internalized by cells in that environment. Such embodiments of the invention allow the targeted delivery of agents such as therapeutic proteins to localized sites of diseased tissue.

The invention disclosed herein has a number of embodiments. One embodiment is a method of forming a protein nanocapsule. In this method, the protein nanocapsule is formed from reagents and under conditions that allow it to have a constellation of material properties that can change in different in vivo environments. In typical embodiments, the method comprises coupling a zwitterionic polymer to a polyallylamine (PAH) to form a PAH conjugate having a zwitterionic moiety. This zwitterion/PAH conjugate is then combined with a protein under conditions that allow the conjugate to self-assemble into a nanocapsule that surrounds the protein. Optionally the protein nanocapsule is further crosslinked with a crosslinking agent. In such embodiments, at a first pH, the zwitterion moiety interacts with charged moieties on the nanocapsule and inhibits uptake of the nanocapsule by macrophages. In addition, in such embodiments, the zwitterion moiety then uncouples from the protein nanocapsule at a pH of less than 6.5, an event which then alters the zeta potential of the remaining PAH structure that encapsulates the protein. This allows the decoupled protein nanocarrier to then be internalized by mammalian cells.

A variety of reagents and processes can be used to form the protein nanocapsules of the invention. Typically the zwitterionic polymer is poly(2-methacryloyloxyethyl phosphorylcholine) (PMPC), and this PMPC is coupled to polyallylamine (PAH) with an acid liable ketal linker to form a zwitterionic PAH-de-PMPC polymer shell. In the working embodiments of the invention that are disclosed herein, the acid liable ketal linker is dithiobis(succinimidyl propionate) (DTSP). Some embodiments of the invention comprise crosslinking the PAH-de-PMPC polymer shell with a crosslinking agent such as di-N-hydroxysuccinimide ester or dithiobis(succinimidyl propionate) (DTSP).

Another embodiment of the invention is a composition of matter comprising a cargo (such a therapeutic or diagnostic protein) encapsulated by a shell comprising a zwitterionic polymer. The shell typically comprises the zwitterionic polymer reversibly coupled to a polyallylamine (PAH). Typically, the zwitterionic polymer shell encapsulates the cargo agent, and remains coupled to the shell at a pH above 7.5 yet the detaches from the PAH at a pH less than 6.5. In some embodiments, the zwitterionic polymer is a poly(2-methacryloyloxyethyl phosphorylcholine) (PMPC) and the PMPC is conjugated with the PAH with an acid liable ketal linker to form a zwitterionic PAH-de-PMPC polymer shell. In certain embodiments, the PAH-de-PMPC polymer shell is crosslinked with a di-N-hydroxysuccinimide ester or dithiobis(succinimidyl propionate) (DTSP). Typically in such embodiments, the cargo agent is a single protein.

Yet another embodiment of the invention is a method of delivering a cargo such as a therapeutic or diagnostic protein into a mammalian cell (e.g. a mammalian tumor cell growing in vivo at a site having a pH of less than 7). Typically, such methods comprise combining a protein nanocapsule with the mammalian cell, the protein nanocapsule comprising a protein and a zwitterionic polymer shell comprising a zwitterionic polymer coupled with a polyallylamine (PAH). In such embodiments, polymer shell having the zwitterionic moieties encapsulates the protein in a manner that inhibits its opsonization by macrophages at a first environmental pH. In these embodiments, the zwitterionic moieties can be decoupled from the PAH shell at a second environmental pH. In illustrative embodiments, the method comprises uncoupling the zwitterionic polymer from the PAH in a manner of that allows the resultant protein nanocarrier to then be internalized by a mammalian cell (e.g. a cancer cell at the site of a tumor).

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
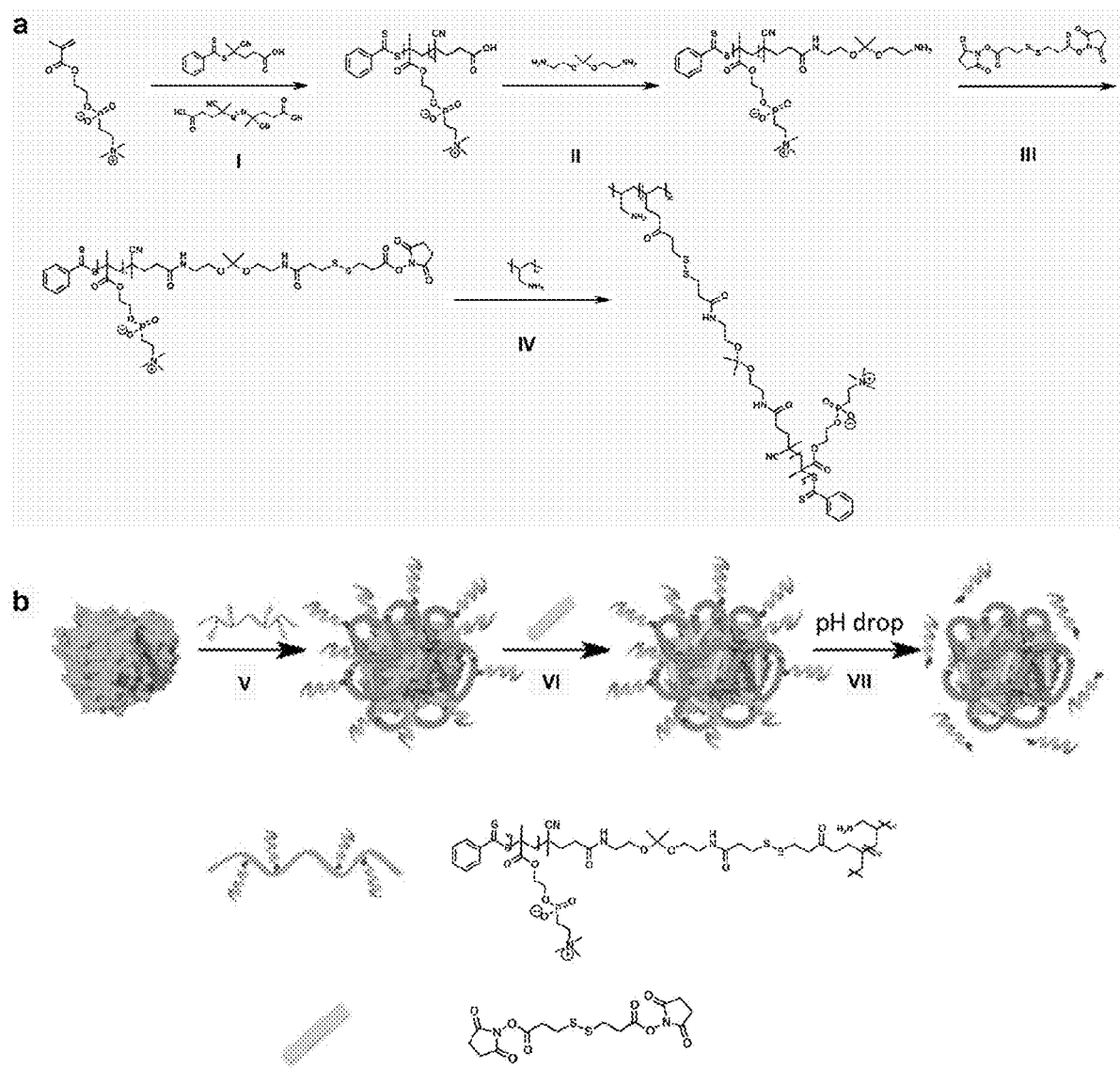
FIG. 1 is a schematic illustration of the synthesis of PAH-de-PMPC and subsequent synthesis of de-nProtein, in accordance with one or more embodiments of the invention.

Many of the techniques and procedures described or referenced herein are well understood and commonly employed using conventional methodology by those skilled in the art. In the description of the preferred embodiment, reference may be made to the accompanying drawings which form a part hereof, and in which is shown by way of illustration a specific embodiment in which the invention may be practiced. It is to be understood that other embodiments may be utilized and structural changes may be made without departing from the scope of the present invention.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The invention disclosed herein has a number of embodiments. One embodiment of the invention is a method of forming a protein nanocapsule. In typical embodiments, the method comprises coupling a zwitterionic polymer to a polyallylamine (PAH) to form a PAH conjugate having a zwitterion moiety. This PAH conjugate is then combined with a protein under conditions that allow the PAH conjugate to self-assemble into a nanocapsule that surrounds the protein. Optionally the protein nanocapsule is further crosslinked with a crosslinking agent. In this method, the protein nanocapsule is formed from reagents and under conditions that allow it to have a constellation of material properties. In such embodiments, the zwitterion moiety interacts with charged moieties on the nanocapsule and inhibits uptake of the nanocapsule by macrophages. In addition, in such embodiments, the zwitterion moiety uncouples from the protein nanocapsule at a pH of less than 6.5, an event which then alters the zeta potential of the remaining structure that encapsulates the protein.

A variety of reagents and processes can be used to form the protein nanocapsules of the invention. Typically, for example, the zwitterionic polymer is a poly(2-methacryloyloxyethyl phosphorylcholine) (PMPC), and this PMPC is coupled to polyallylamine (PAH) with an acid liable ketal linker to form a zwitterionic PAH-de-PMPC polymer shell. In the working embodiments of the invention that are disclosed herein, the acid liable ketal linker is dithiobis (succinimidyl propionate) (DTSP). Optionally, the zwitterionic polymer is synthesized by reversal additional fragmentation transfer (RAFT) polymerization using 2-methacryloyloxyethyl phosphorylcholine (MPC) as a monomer, 4-cyano-4-(phenylcarbonothioylthio) pentanoic acid as a chain transfer agent (CTA), and 4,4'-azobis(4-cyanovaleric acid) (ACVA) as an initiator. In certain embodiments of the invention, the PMPC is further conjugated with 2,2-bis(aminoethoxy)propane prior to conjugation with the PAH.

Some embodiments of the invention further comprise crosslinking the PAH-de-PMPC polymer shell with a crosslinking agent such as di-N-hydroxysuccinimide ester or dithiobis(succinimidyl propionate) (DTSP). Other crosslinking agents can be used, for example a crosslinking agent comprising a peptide having an amino acid sequence that is cleaved by a protease. In some embodiments, the crosslinker is a degradable crosslinker. A degradable crosslinker is cleaved under certain conditions, resulting in decomposition or removal of at least a portion of the polymer shell of the nanocapsule. For example, a degradable crosslinker may hydrolyze at certain pH (high or low), may be cleaved by specific enzymes (such as esterases or peptidases), may be photolytically cleaved upon exposure to certain wavelengths, or be cleaved at certain temperatures. Examples of crosslinkers which hydrolyze at reduced pH include glycerol dimethacrylate, which is stable at physiological pH (about 7.4), but hydrolyzes at lower pH (about 5.5). Other examples of degradable crosslinkers include acetal crosslinkers described in U.S. Pat. No. 7,056,901, which is incorporated by reference in its entirety.

Another embodiment of the invention is a composition of matter comprising a cargo such a therapeutic or diagnostic protein encapsulated by a zwitterionic polymer having a constellation of material properties. These properties include a shell comprising a zwitterionic polymer reversibly coupled to a polyallylamine (PAH). Typically, the zwitterionic polymer shell encapsulates the cargo agent, and remains coupled to the PAH shell at a pH above 7.5 yet the detaches from the PAH at a pH less than 6.5. In some embodiments, the zwitterionic polymer is a poly(2-methacryloyloxyethyl phosphorylcholine) (PMPC) and the PMPC is conjugated with the PAH with an acid liable ketal linker to form a zwitterionic PAH-de-PMPC polymer shell. In certain embodiments, the PAH-de-PMPC polymer shell is crosslinked with a di-N-hydroxysuccinimide ester or dithiobis (succinimidyl propionate) (DTSP). Typically in such embodiments, the cargo agent is a single protein such as a growth factor (e.g. vascular endothelial growth factor) or a protein that induces apoptosis (e.g. tumor necrosis factor).

Yet another embodiment of the invention is a method of delivering a cargo such as a therapeutic or diagnostic protein into a mammalian cell, for example a mammalian tumor cell growing in an in vivo environment having a pH of less than 7. Typically such methods comprise combining a protein nanocapsule with a mammalian cell, the protein nanocapsule comprising a protein and a zwitterionic polymer shell comprising a zwitterionic polymer coupled with a polyallylamine (PAH). In such embodiments, polymer shell having the Zwitterionic moieties encapsulates the protein in a manner that inhibits its opsonization by macrophages. In these embodiments, the zwitterionic moieties can be decoupled from the PAH shell (e.g. the PMPC decouples from the PAH at a pH below 6.5). In such embodiments, the method comprises uncoupling the zwitterionic polymer from the PAH in a manner of that allows the resultant protein nanocarrier to then be internalized by the mammalian cell.

Zwitterionic polymers useful in embodiments of the invention include for example poly 2-methacryloyloxyethyl phosphorylcholine (MPC), poly sulfobetaine methacrylate (SBMA) and poly carboxybetaine methacrylate (CBMA). Optionally in these embodiments, the zwitterionic polymer is a poly(2-methacryloyloxyethyl phosphorylcholine) (PMPC) and the PMPC is coupled with the PAH with an acid liable ketal linker such as dithiobis(succinimidyl propionate) (DTSP) to form a zwitterionic PAH-de-PMPC polymer shell. In certain embodiments, the PAH-de-PMPC polymer shell is further crosslinked with an agent such as di-N-hydroxysuccinimide ester or dithiobis(succinimidyl propionate) (DTSP).

As noted above, embodiments of the invention provide a poly(2-methacryloyloxyethyl phosphorylcholine) (PMPC) zwitterionic polymer synthesized by reversal addition fragmentation transfer (RAFT) polymerization and further conjugated with a polyallylamine (PAH) backbone through an acid liable ketal linker. The resulting PAH-de-PMPC can self-assemble with proteins and be further crosslinked by di-N-hydroxysuccinimide esters to form protein nanocapsules denoted as de-nProtein. These nanocapsules provide a suitable platform for protein therapeutics with a prolonged circulation time and the ability to be delivered into targeted cells. In one aspect, a protein nanocapsule is provided which comprises a protein core and a polymer shell with poly(2-methacryloyloxyethyl phosphorylcholine) (PMPC) grafted polyallylamine hydrochloride (PAH) through an acid liable ketal linker (PAH-de-PMPC). At physiological pH, the PMPC forms a hydration layer that shields the nanocapsule from opsonization and macrophage uptake. However, in an acidic environment, for instance when the pH drops to pH 6.5 or lower, the PMPC detaches from the PAH backbone. The resulting positively charged nanocapsules may then be internalized by cells.

Figure 2:
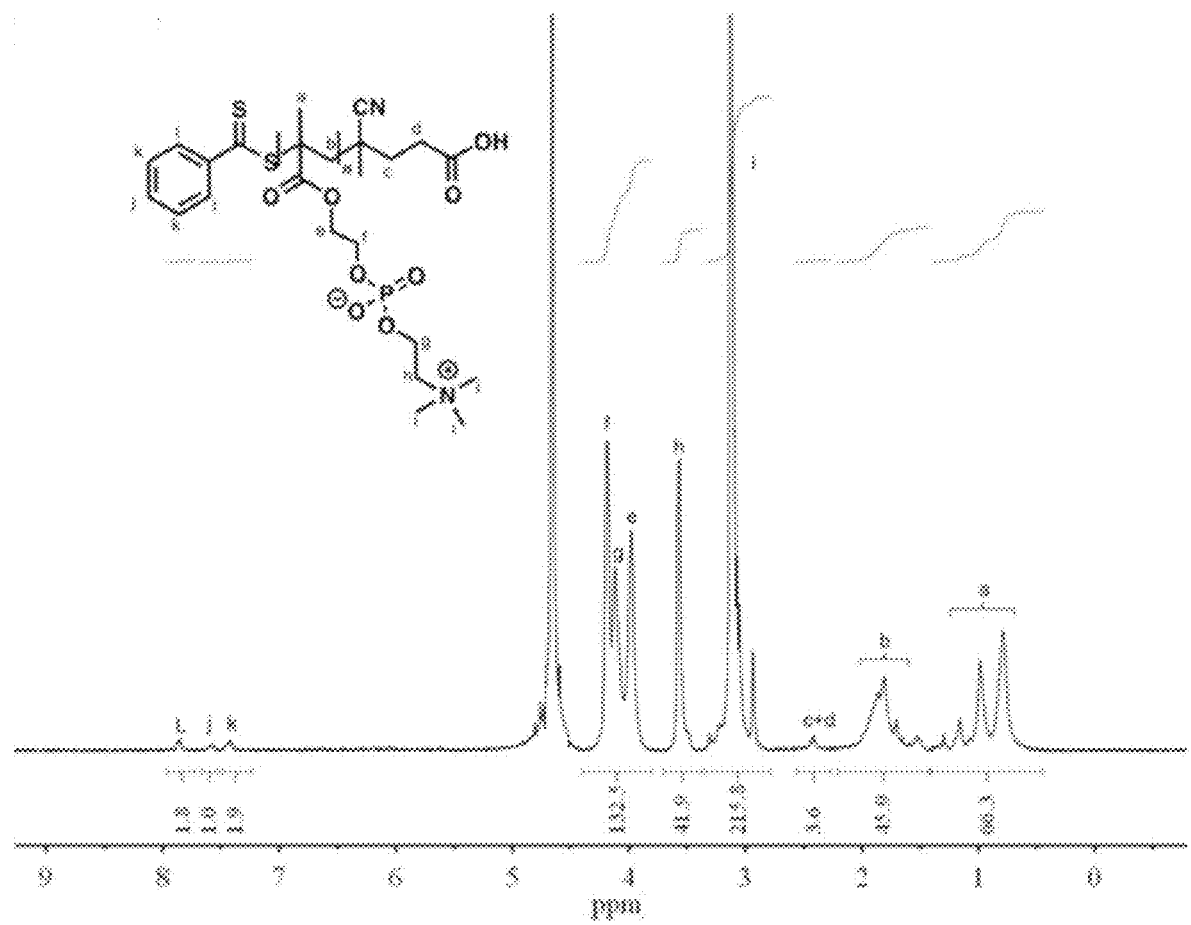
FIG. 2 illustrates the H'NMR spectrum of PMPC, in accordance with one or more embodiments of the invention.

In another aspect, a method of synthesizing a protein nanocapsule is provided. In one or more embodiments, as illustrated in FIG. 1, a PMPC zwitterionic polymer is synthesized by reversal addition fragmentation transfer (RAFT) polymerization (Step I) using 2-methacryloyloxyethyl phosphorylcholine (MPC) as a monomer, 4-cyano-4-(phenylcarbonothioylthio) pentanoic acid as a chain transfer agent (CTA), and 4,4'-azobis(4-cyanovaleric acid) (ACVA) as an initiator. In an illustrative experiment, the successful synthesis of PMPC with 20 units per polymer chain was verified by H'NMR spectrum (FIG. 2). The carboxyl group on the polymer end is further conjugated with 2,2-bis (aminoethoxy)propane through an EDC/NHS reaction (Step II), and subsequently conjugated with PAH through dithiobis (succinimidyl propionate) (DTSP) (Step III and IV). Self-assembly of protein and PAH-de-PMPC results in the formation of protein nanocapsules (denoted as de-nProtein) (Step V) which are further crosslinked by DTSP (Step VI).

Figure 3:
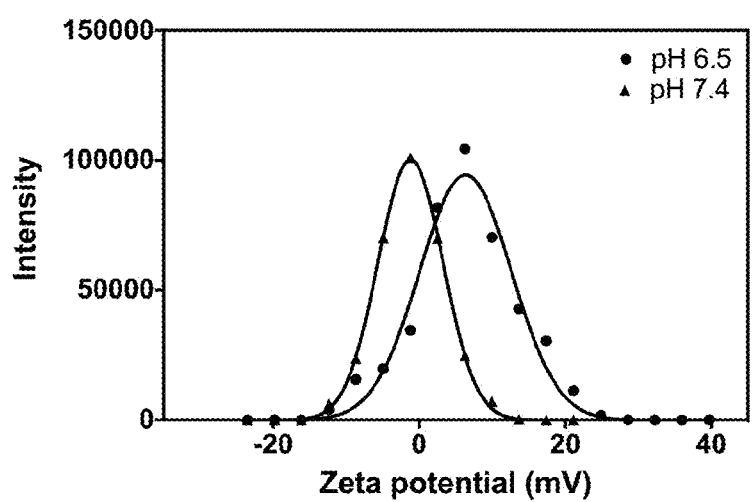
FIG. 3 illustrates the zeta potential distribution of de-nBSA before and after incubation at pH 6.5 for 2 hours, in accordance with one or more embodiments of the invention.
Figure 4:
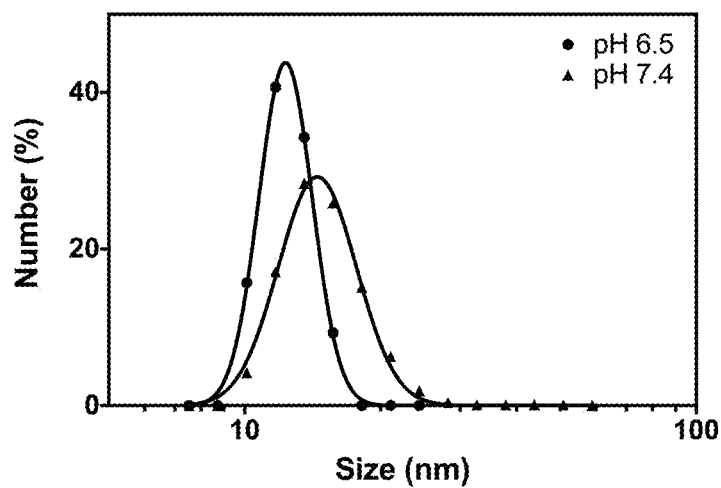
FIG. 4 illustrates the size distribution of de-nBSA before and after incubation at pH 6.5 for 2 hours, in accordance with one or more embodiments of the invention.

In an illustrative experiment using bovine serum albumin (BSA) as a model protein, the successful synthesis of de-nBSA was characterized by zeta potential and DLS measurement. FIG. 3 presents the zeta potential distribution of de-nBSA. The zeta potential of the de-nBSA centered at 0 mV, significantly different from the native BSA (−7 mV), indicating that the successful shielding of charges on the nanocapsules due to PMPC attachment. However, after the de-nBSA was incubated at pH 6.5, the zeta potential shift to +7 mV, demonstrating that the positive charge on the PAH backbone was exposed after the detachment of PMPC. Consistent with zeta potential analysis, the size distribution measured by dynamic light scattering (DLS) (FIG. 4) also confirms the uniform size of de-nBSA around 14 nm at pH 7.4, significantly different from that of the native BSA (5 nm). After incubation at pH 6.5, the size deceased to 12 nm, which can be attributed to the smaller hydraulic radius after the detachment of hydrophilic PMPC with a large hydration layer.

Figure 5:
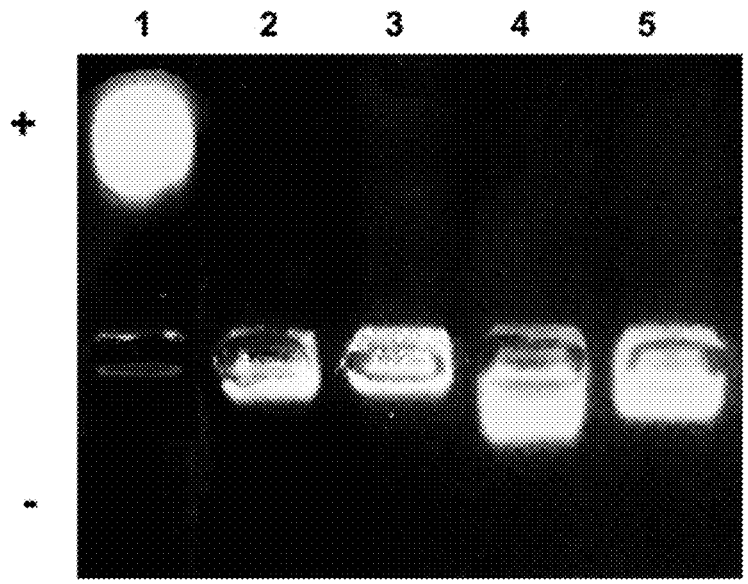
FIG. 5 illustrates an agarose gel analysis of native BSA (1), non-nBSA after incubation at pH 6.5 (2), at pH 7.4 (3), de-nBSA after incubation at pH 6.5 (4) and at pH 7.4 (5), in accordance with one or more embodiments of the invention.

The formation of de-nBSA was further demonstrated by agarose gel analysis. Non-detachable PAH-non-PMPC was also synthesized. The self-assembly of protein and PAH-non-PMPC and subsequent crosslinking by DTSP lead to the formation of protein nanocapsules denoted as non-nProtein. For one instance, nanocapsules with non-detachable PMPC that encapsulate BSA were synthesized (i.e. non-nBSA). As illustrated in FIG. 5, both fluorescein isothiocyanate (FITC) labeled non-nBSA (2 and 3) and de-nBSA (4 and 5) showed retention in the well, which is significantly different from the FITC labeled native BSA bearing negative charge moving towards the anode. After incubation at pH 6.5 (2 and 4), the non-nBSA didn't show charge change (2 and 3). Nevertheless, de-nBSA obviously gained positive charges, as significant movement towards cathode was shown. This further confirms the results of zeta potential analysis that PMPC shielding layer is detached from the nanocapsules. This pH sensitive property allows de-nProtein to provide targeted protein delivery towards the acidic microenvironment of tumor sites.

EXAMPLES

Example 1: Macrophage Uptake of Native BSA, De-nBSA and Non-nBSA

Figure 6:
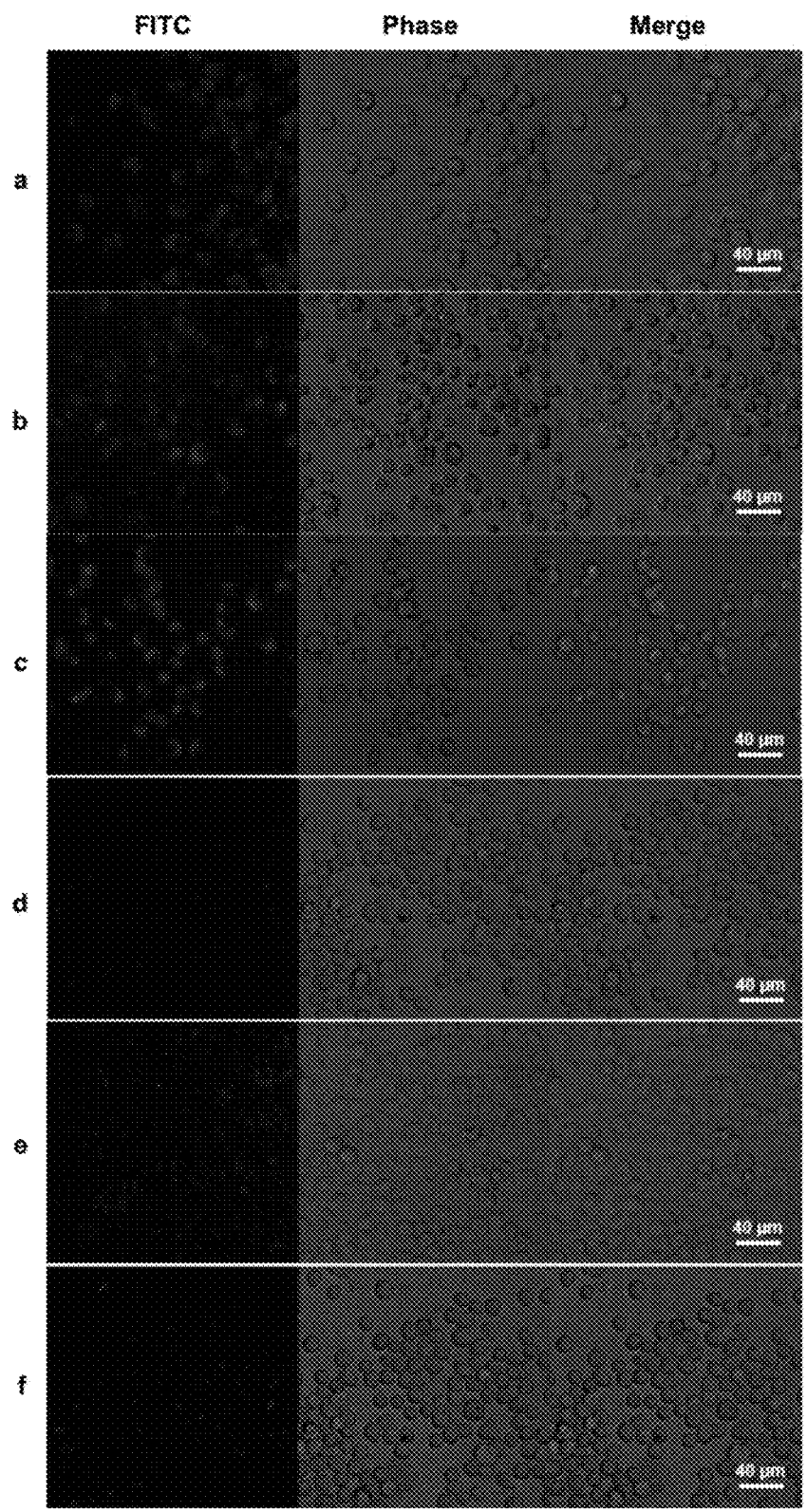
FIG. 6 illustrates native BSA incubated in a) pH 6.5 and b) pH 7.4 medium; de-nBSA incubated in c) pH 6.5 and d) pH 7.4 medium; non-nBSA incubated in e) pH 6.5 and d) pH 7.4 medium, in accordance with one or more embodiments of the invention.

Nanoparticles can easily be opsonized in the blood circulation and uptake by macrophages in the liver and spleen before they can ever reach the targeted site. Thus, escape from opsonization and macrophage uptake is the most important issue for targeted delivery of proteins. In this example, macrophage escape capability was tested using a J774A.1 cell line, which is reticulum macrophage cells from ascites of BALB/cN mice. As is shown in FIG. 6, FITC labeled native BSA showed similar moderate uptake by J774A.1 both under pH 6.5 and pH 7.4 after incubation with mouse serum (FIG. 6 a and b). Nevertheless, macrophage uptake was significantly reduced when non-nBSA was incubated with macrophage and mouse serum both at pH 6.5 and pH 7.4 (FIG. 6 e and f). This indicates the great shielding ability of PMPC hydration layer on the nanocapsule surface and that the non-nProtein could be applied for delivery of proteins which need long circulation, such as removal of uric acid or alcohol in the case of gout treatment or alcohol intoxication. On the other hand, de-nBSA also showed reduced macrophage uptake at pH 7.4 (FIG. 6 d), but after being incubated at pH 6.5 (FIG. 6 c), significant macrophage uptake can be observed. This result further demonstrates the successful detachment of the PMPC side chains from the PAH backbones by acid liable ketal linker. This approach provides suitable platforms for protein therapeutics with prolonged circulation time with the ability of being delivered into the cells.

Example 2: Methods

Synthesis of PMPC by Reversible Addition Fragmentation Chain Transfer (RAFT) Polymerization A mixed solution with monomer/CTA/initiator molar at a ratio of 20:1:0.2 was prepared by dissolving 0.148 g MPC, 7 mg 4-cyano-4-(phenylcarbonothioylthio) pentanoic acid and 1.4 mg ACVA in a mixture of 0.2 mL dimethylformamide (DMF) and 0.4 mL methanol. The solution was degassed by three freeze-pump-thaw cycles and purged with nitrogen to remove oxygen. The degassed solution was set at 60° C. for 6 hours and the resulting PMPC was diluted with 1 mL methanol and precipitated and washed with tetrahydrofuran (THF). The resulting PMPC has about 20 units per polymer chain, as determined by H'NMR spectrum.

Synthesis of PMPC Conjugated PAH with Acid Liable Linker (PAH-De-PMPC)

The activation of PMPC was done by EDC/NHS activation. Briefly, 0.1 g PMPC was dissolved in 1 mL methanol followed by adding 33 mg EDC (10× molar excess) and 2 mg NHS. The active PMPC-NHS ester was further reacted with 5× molar excess of ketal linker, 2,2-bis(aminoethoxy) propane (13 mg). The resulting ketal-PMPC was purified by precipitation in THF to remove the excess 2,2-bis(aminoethoxy)propane, EDC and NHS. The purified ketal-PMPC was reacted with 5× molar excess of dithiobis(succinimidyl propionate) (DTSP) in methanol with triethylamine as acid binding agent. The resulting NHS ester of ketal-PMPC was further purified by precipitation in THF. Subsequent reaction with PAH resulted in PMPC conjugated PAH (PAH-de-PMPC), which is detachable under an acidic environment. A non-detachable PMPC conjugated PAH (PAH-non-PMPC) was also synthesized by direct reaction between PAH and PMPC-NHS.

Synthesis of PMPC Grafting Nanocapsules

BSA was dialyzed against 10 mM pH 8.0 phosphate buffer. Subsequently, BSA was mixed with aqueous solution of PAH-de-PMPC at a molar ratio of 1:15 and self-assembled to nanocomplexes. The nanocomplexes were further crosslinked by reaction with DTSP at a BSA/DTSP ratio of 1:100 to form de-nBSA. The nondetachable PAH-non-PMPC was also self-assembled with BSA and further crosslinked by DTSP to make non-nBSA.

DLS Measurement

DLS experiments were performed with a Zetasizer Nano-ZS (Malvern Instruments Ltd., UK) equipped with a 10-mW helium-neon laser ($\lambda$=632.8 nm) and thermoelectric temperature controller. Measurements were taken at a 173° scattering angle. The de-nBSA was incubated both at pH 7.5 and pH 6.5 phosphate buffer, respectively, for 2 hours and zeta potential and size distribution were further measured at pH 7.5 at a protein concentration of 0.5 mg/mL at 25° C.

In Vitro Macrophage Escape and Uptake Measurement

Cellular internalization studies were assessed via fluorescence microscopic technique. Murine macrophage J774A.1 was cultured in Dulbecco's modified Eagle's medium (DMEM) supplemented with 10% fatal bovine serum (FBS) and 1% penicillin/streptomycin. Cells (5000 cells/well, 96-well plate) were seeded the day before adding the nanocapsules. Native BSA, de-nBSA and non-nBSA were added into the cell medium with different pH at a final BSA concentration of 0.05 mg/ml. After incubation at 37° C. for 4 hours, the cells were washed three times with PBS and visualized with an Carl Zeiss Axio Observer inverted fluorescence microscope.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

All publications, patents, and patent applications cited herein are hereby incorporated by reference in their entirety for all purposes.

The invention claimed is:

1. A method of delivering a protein into a mammalian cell, the method comprising:
    combining a protein nanocapsule with a mammalian cell, the protein nanocapsule comprising:
        a protein; and
        a zwitterionic polymer shell that encapsulates the protein, the polymer shell comprising a zwitterionic polymer coupled with a polyallylamine (PAH); wherein:
        the zwitterionic polymer comprises a poly(2-methacryloyloxyethyl phosphorylcholine) (PMPC);
        the zwitterionic polymer is coupled to the PAH at a first pH, wherein the first pH is 7.4; and
        the zwitterionic polymer uncouples from the PAH at a second pH, wherein the second pH is 6.5; and
    uncoupling the zwitterionic polymer from the PAH so that the resulting protein nanocarrier is internalized by the mammalian cell.

2. The method of claim 1, wherein the PMPC is coupled with the PAH with an acid liable ketal linker to form a zwitterionic PAH-de-PMPC polymer shell.

3. The method of claim 2, wherein the PAH-de-PMPC polymer shell is further crosslinked with a di-N-hydroxysuccinimide ester or dithiobis(succinimidyl propionate) (DTSP).

4. The method of claim 1, wherein the mammalian cell is in vivo at a site having a pH of less than 7.

5. The method of claim 2, wherein the acid liable ketal linker is dithiobis(succinimidyl propionate) (DTSP).

6. The method of claim 1, wherein the protein is delivered to the mammalian cell in vivo.

7. The method of claim 4, wherein the site is a tumor site and the mammalian cell is a cancer cell.

* * * * *